United States Patent [19]

Kierstead et al.

[11] 4,152,424

[45] May 1, 1979

[54] ANTIBIOTIC 1745A/X AND METHODS FOR THE PRODUCTION THEREOF

[75] Inventors: Richard W. Kierstead; Ronald A. LeMahieu, both of North Caldwell; David Pruess, Passaic, all of N.J.

[73] Assignee: Hoffmann-La Roche Inc., Nutley, N.J.

[21] Appl. No.: 887,160

[22] Filed: Mar. 16, 1978

Related U.S. Application Data

[60] Continuation of Ser. No. 761,922, Jan. 24, 1977, abandoned, which is a continuation of Ser. No. 598,483, Jul. 23, 1975, abandoned, which is a division of Ser. No. 438,987, Dec. 23, 1975, Pat. No. 3,928,387.

[51] Int. Cl.² .......................................... A61K 35/00
[52] U.S. Cl. .................................. 424/120; 195/80 R
[58] Field of Search ...................... 424/120; 195/80 R

[56] References Cited

U.S. PATENT DOCUMENTS

| | | | |
|---|---|---|---|
| 3,361,737 | 1/1968 | Jones | 536/9 |
| 3,478,014 | 11/1969 | Djokic et al. | 536/9 |
| 3,674,773 | 5/1972 | Kurath | 536/9 |
| 3,697,547 | 10/1972 | Kurath et al. | 536/9 |

*Primary Examiner*—Jerome D. Goldberg
*Attorney, Agent, or Firm*—Jon S. Saxe; Bernard S. Leon; Frank P. Hoffman

[57] ABSTRACT

A new antibiotic, designated as antibiotic 1745A/X, is produced by the fermentation of the known microorganism *Streptomyces antibioticus*, ATCC 11891, using the novel compound erythronolide A oxime as the substrate. This new antibiotic is useful an an antibacterial agent.

1 Claim, 2 Drawing Figures

ANTIBIOTIC 1745A/X AND METHODS FOR THE PRODUCTION THEREOF

DETAILED DESCRIPTION OF THE INVENTION

Figure 1:
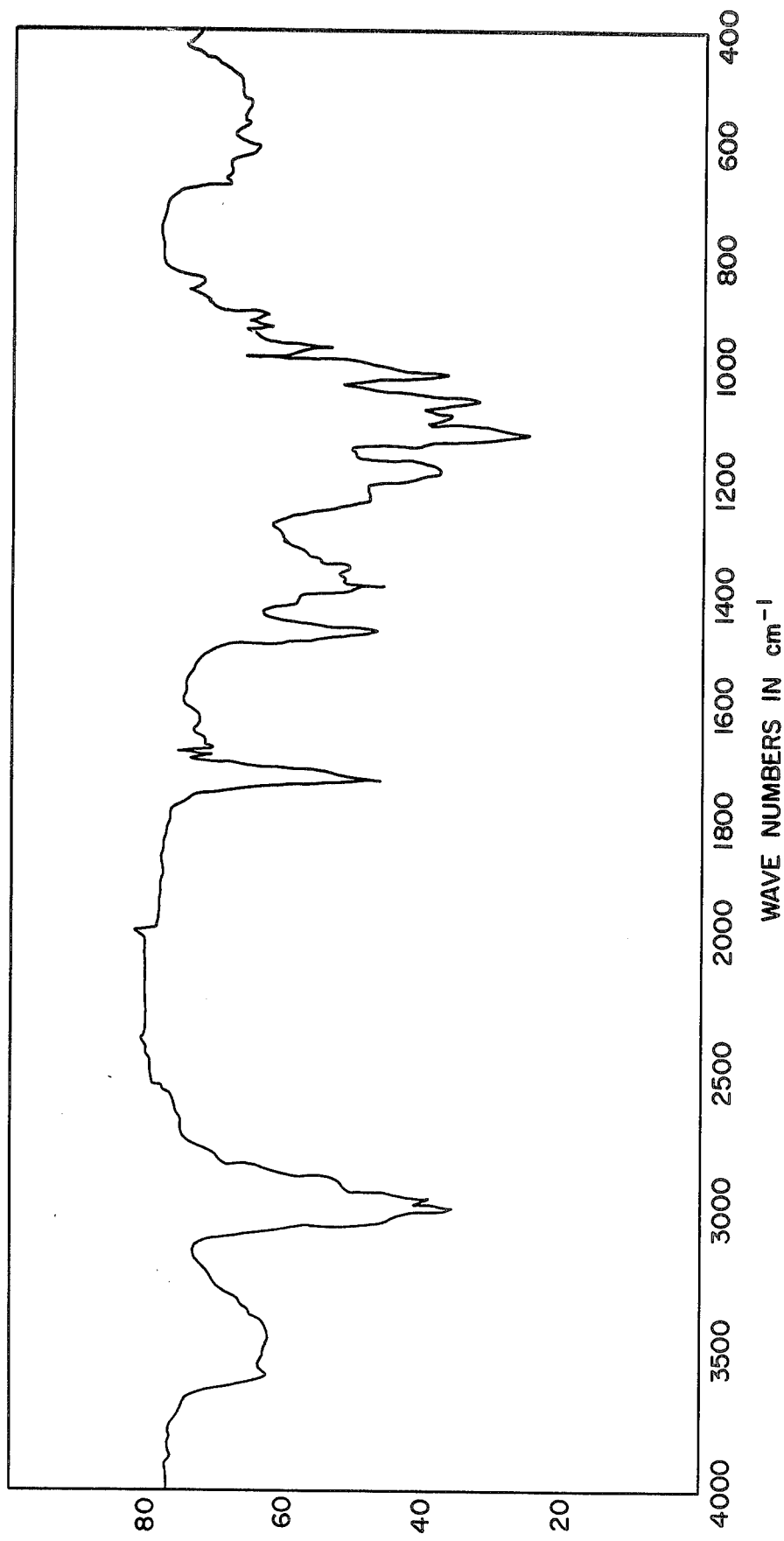

This is a continuation, of application Ser. No. 761,922 filed Jan. 24, 1977 now abandoned which in turn is a continuation of application Ser. No. 598,483, filed July 23, 1975 now abandoned, which in turn is a divisional of U.S. patent application Ser. No. 438,987, now U.S. Pat. No. 3,928,387, issued Dec. 12, 1975.

This invention relates to a new antibiotic and to methods for its production by fermentation, its isolation and purification, and its use as an antibacterial agent. The present invention includes within its scope the antibiotic 1745A/X in pure form, in dilute forms, and as a crude concentrate.

The new antibiotic, designated hereinafter as antibiotic 1745A/X, is produced by the fermentation of the known microorganism *Streptomyces antibioticus,* ATCC 11891, using as the substrate the novel compound erythronolide A oxime. The species of Streptomyces described herein and identified as *Streptomyces antibioticus,* ATCC 11891 includes all strains of Streptomyces which when fermented under the conditions described herein produce antibiotic 1745A/X and which cannot be definitely differentiated from the strain ATCC 11891 and its subcultures, including mutants and variants. By the term "mutants" as used herein, there is intended mutants produced from the described organism by various means such as chemical mutagenic agents, ultra-violet radiation, X-radiation, phage exposure and the like.

As described above, antibiotic 1745A/X is produced by the fermentation of *Streptomyces antibioticus,* ATCC 11891, using as the substrate in the fermentation the novel compound erythronolide A oxime. This compound is prepared by the cleavage of the cladinose and desosamine sugar moieties from the known oxime of of erythromycin A of the formula

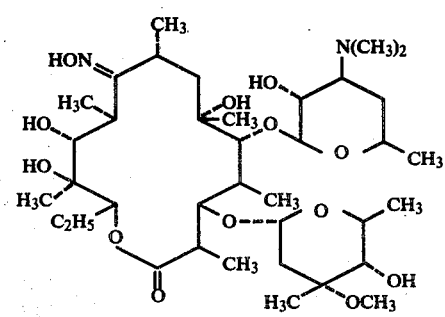

Cleavage of the cladinose and desosamine sugar moieties from the oxime of formula I is accomplished by first converting the oxime to the corresponding N-oxide of the formula

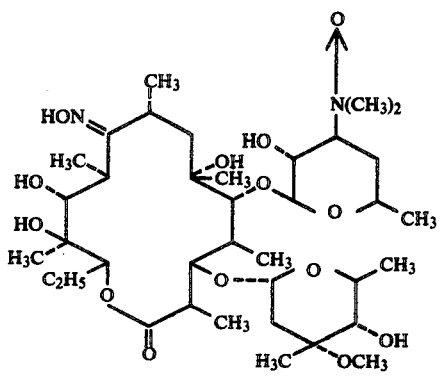

Conversion of the oxime of formula I above to the corresponding N-oxide of formula II is accomplished by treating the oxime with hydrogen peroxide. This reaction is preferably effected in the presence of an inert organic solvent. Suitable solvents include lower alkanols such as methanol, ethanol, propanol and the like. It is expedient to effect this reaction at a temperature in the range of from 0° to about 40° C., with room temperature being preferred.

The so-obtained N-oxide of formula II is then converted to the corresponding des-(dimethyamino-N-oxide) compound of the formula

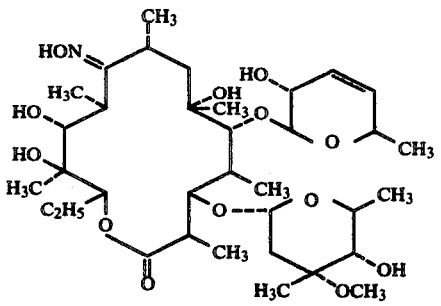

Conversion of the compound of formula II to the compound of formula III is effected by pyrolysis of the N-oxide. This pyrolysis is carried out under vacuum (about 0.1 mm) using a temperature between 150°–160° C.

The so-obtained compound of formula III is then converted to erythronolide A oxime of the formula

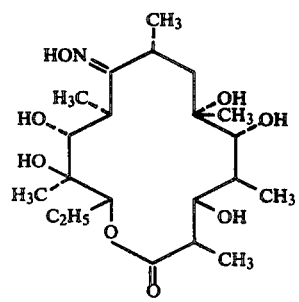

Cleavage of the cladinose and the modified desosamine sugar moieties from the compound of formula III is accomplished by treating said formula III compound with a mineral acid. Suitable mineral acids for this purpose include hydrochloric acid, hydrobromic acid and sulfuric acid. This reaction is preferably effected in the presence of an inert organic solvent. Examples of solvents that can be employed for this reaction include lower alkanols such as methanol, ethanol, propanol and the like. Temperatures in the range of from about 0° to about 30° C. can be employed for the reaction, with room temperature being preferred.

The compounds of formulae II, III and IV are novel and as such form a part of the present invention.

Cultivation of the organism *Streptomyces antibioticus*, ATCC 11891, using erythronolide A oxime as the substrate to produce the desired antibiotic 1745A/X may be carried out utilizing a variety of fermentation techniques. In general, the following basic techniques can be employed in both flask and tank procedures. In the flask fermentation, a loopful of spores from an agar slant of the culture is inoculated into 100 ml. of nutrient medium in a 500 ml. Erlenmeyer flask and incubated at about 28° C. on a rotary shaker for up to 3 days. The inoculation nutrient medium contains a nitrogen source, preferably selected from an acid or enzyme hydrolyzed protein source such as enzyme hydrolyzed milk products, enzyme hydrolyzed bean meal products and the like; a carbohydrate source such as glucose, sucrose, molasses, and the like; and inorganic salts such as phosphate and sulfate salts, sodium chloride, and the like. A preferred inoculum medium is the thermoactinomyces Beer Medium VI broth (*J. Appl. Micro biol.*, 9, 394–399, 1961) distributed by Difco Laboratories, Detroit, Mich. After incubation in the inoculum medium for up to three days small samples of the broth are transferred to the culture medium where they are incubated at about 28° C. on a rotary shaker. After incubation for up to 10 hours, erythronolide A oxime is added to the culture medium as the substrate and incubation is continued for from about 1 to 5 days. Whole broth samples are aseptically removed periodically for determination of the course of fermentation. For preparation of larger volumes of broth, inoculum is first prepared in 6 liter Erlenmeyer shake flasks or in 5 gallon pyrex bottles, fitted for aeration, sampling, etc. This broth is then transferred to the tank fermentors. Aeration in bottles and tanks is provided by forcing sterile air through the fermenting medium. In tanks, further agitation is provided by mechanical impellers. Antifoam agents such as lard oil, soy bean oil, silicone surfactants such as SAG #4130 (Union Carbide Corp.) and DCAF (Dow-Corning) are added as needed to control foam.

*Streptomyces antibioticus*, ATCC 11891 may be cultured in a variety of liquid culture media. Media which are especially useful for the purposes of the present invention include an assimilable carbon source such as starch, glucose, sucrose, molasses, glycerol, dextrin, corn starch, and the like, and an assimilable nitrogen source such as protein, protein hydrolysate, polypeptides, amino acids, corn steep liquor and the like. Complex nitrogenous material from varying sources will support production of antibiotic 1745A/X. Examples of such include plant materials such as soybean flour, animal materials such as meat meal digest, and microbial materials such as yeast. Inorganic cations and anions, such as potassium, sodium, calcium, magnesium, sulfate, phosphate, chloride, etc. can also be added to the culture medium. In addition, those elements such as cobalt, copper, iron, molybdenum, boron, etc. can be added if they are not supplied as impurities of other constituents of the media.

The activity of antibiotic 1745A/X can be measured in vitro by its zone of inhibition against the microorganisms *Sarcina lutea* PCI in the standard paper-disc agar diffusion method. Inoculum was prepared from *Sarcina lutea* PCI grown for 20–24 hours in 100 ml of broth containing Bacto-peptone 6 g/l, cerelose 1 g/l, N-Z amine A 4 g/l, yeast autolysate 3 g/l and beef extract 1.5 g/l. in a 500 ml cotton-plugged Erlenmeyer flask at 35° C. on a rotary shaker at 240 RPM. A portion of the cells were inoculated into molten agar (containing the same ingredients as the above-defined broth with the addition of agar—15 g/l). The molten agar was then poured into either 16×35.5 cm steel covered glass assay pans or 12×88 cm plastic petri dishes and allowed to solidify. Broth samples of partially purified samples of antibiotic 1745A/X were applied to 6.5 mm diameter discs which were then placed on the agar. After incubation overnight at 37° C. the diameters of the zones of inhibition were measured. The zone diameters were found to be proportional to the log of the concentration between 3.0 and 100 mcg. per ml. of antibiotic 1745A/X. A two-fold increase in the concentration of antibiotic 1745A/X increased the zone diameter by 2.7 mm.

After fermentation is complete, a variety of procedures can be employed for the isolation and purification of antibiotic 1745A/X. Suitable isolation and purification procedures include solvent extraction techniques, such as batchwise extraction or countercurrent continuous flow liquid-liquid extraction columns, and gel permeation chromatography. In a preferred process, antibiotic 1745A/X is recovered from the culture medium by separation of the mycelium and any undissolved solids from the fermentation broth by conventional means such as by filtration or centrifugation. Antibiotic 1745A/X is then extracted from the filtered or centrifuged broth using either batchwise or counter current distribution extraction techniques. The solvent extraction may be performed using a pH range of from 8 to 10 and employing as the solvent an inert organic solvent. Suitable solvents include alcohols, such as methanol, ethanol and the like, chlorinated hydrocarbons such as chloroform, methylene chloride and the like, ethyl acetate, butyl acetate, amyl acetate, acetone and acetonitrile, with methylene chloride being preferred. Final purification of antibiotic 1745A/X can be achieved by chromatography on permeable gels. This purification technique is accomplished by percolation of prepurified preparations of the antibiotic, for example, preparations obtained by solvent extraction techniques, through cross-linked polymerized dextran gels. In a preferred aspect of this purification technique, the pre-purified antibiotic preparation is chromatographed on Sephadex G-25 eluting with n-butanol/acetic acid/water.

After filtration or centrifugation of the fermentation medium, thin layer or paper chromatography techniques can be employed to analyze for antibiotic 1745A/X. In addition, bioautography can also be employed advantageously.

The novel antibiotic of the invention, antibiotic 1745A/X, upon purification, exists in crystalline form, m.p. 146°–149° C. From elemental analysis of the free base and the methiodide salt of antibiotic 1745A/X, the formula $C_{36}H_{66}N_2O_{13}$ was assigned to the antibiotic. The antibiotic contains the elements carbon, hydrogen, nitrogen and oxygen in substantially the following percentages by weight:

|  | Antibiotic 1745A/X |
| --- | --- |
| Carbon | 58.69 |

| | Antibiotic 1745A/X | |
|---|---|---|
| Hydrogen | 9.26 | |
| Nitrogen | 3.45 | |
| Oxygen | 28.60 | (by difference) |

The following are various physical characteristics of antibiotic 1745A/X:

The infrared absorption spectrum of antibiotic 1745A/X 4% chloroform solution is shown in FIG. 1. The antibiotic exhibits characteristic absorption in the infrared region of the spectrum at the following wave lengths expressed in reciprocal centimeters:

Broad band at 3500
Complex absorption at 3000
Prominent bands at 1735, 1470, 1180, 1120, 1060 and 1000.

The low resolution mass spectrum of antibiotic 1745A/X shows a molecular ion at m/e 734 and major fragment peaks at 701, 649, 617, 573, 560, 546, 462, 416, 398, 251, 174, 158 and 145.

Figure 2:
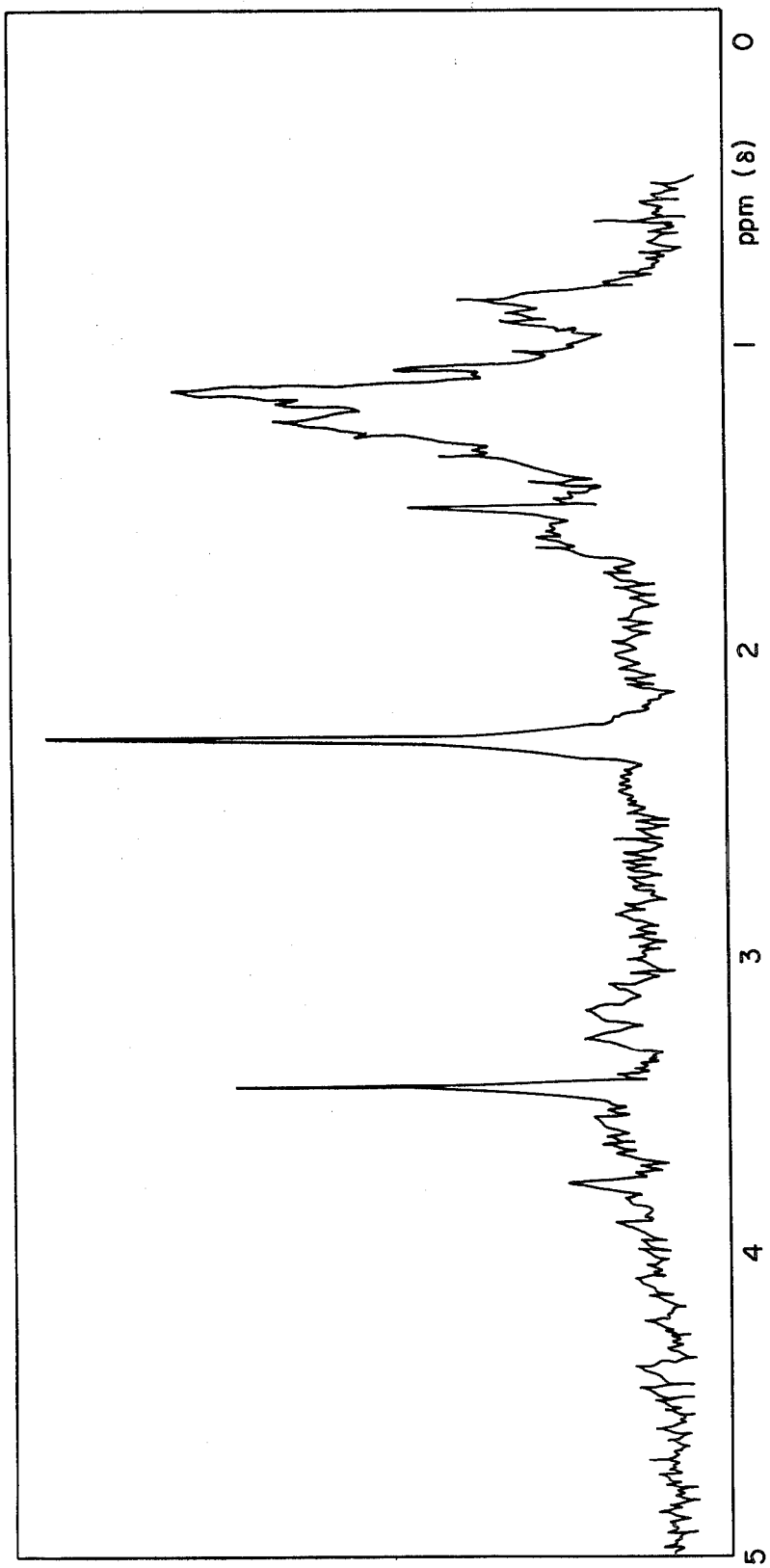
Figure 2:
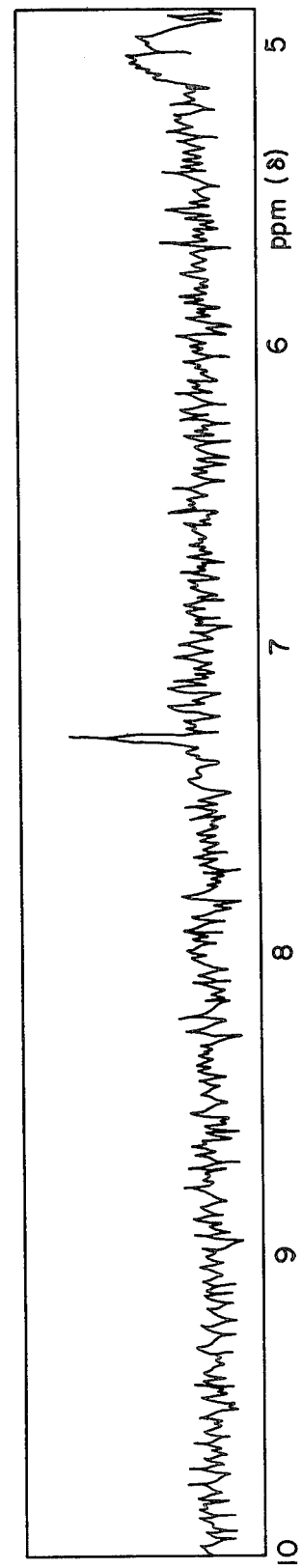

The nuclear magnetic resonance spectrum of antibiotic 1745A/X is shown in FIG. 2. The NMR spectrum was obtained using $CDCl_3$ as the solvent and tetramethylsilane (TMS) as the internal standard. The NMR spectrum exhibits prominent signals at $3.42\delta$, $2.28\delta$, $1.16\delta$ and in the region between $0.8$ and $1.7\delta$.

Antibiotic 1745A/X exhibits antimicrobial activity against gram positive microorganisms as shown in Table 1. The antimicrobial spectrum was determined by employing agar diffusion paper-disc assays as described earlier.

TABLE 1

*In Vitro* Animicrobial Spectrum
Antibiotic 1745A/X

| Test Organism* | Diameter of Inhibition Zones in mm. (Antibiotic 1745A/X in 3A alcohol-discs dipped and air dried) | | |
|---|---|---|---|
| | 10 mcg/ml | 100 mcg/ml | 1mg/ml |
| *Bacillus subtilis* | 0 | 12 | 22 |
| *Sarcina lutea* | 8 | 19 | 28 |
| *Mycobacterium phlei* | 0 | 12 | 19 |
| *Bacillus sp.* 1283 (B(TA) | 0 | 13.5 | 22 |

*Microorganism grown in broth containing Bactopeptone-6g/l., cerelose-1g/l., M-Z amine A-4g/l., yeast artolysate-3g/l., and beef extract -1.5g/l.

As indicated above, antibiotic 1745A/X is useful as an antimicrobial agent. Thus, this compound can be used as a medicament. For example, it can be used in the form of pharmaceutical preparations which contain it in admixture with a pharmaceutical organic or inorganic carrier material which is suitable for enteral or parenteral application such as, for example, water, gelatin, lactose, starches, magnesium stearate, talc, vegetable oils, gum arabic, polyalkylene glycols, vaseline, etc. The pharmaceutical preparations can be prepared in solid form (e.g., as tablets, dragees, suppositories, capsules) or in liquid form (e.g., as solutions, suspensions or emulsions). They may be sterilized and/or contain additives such as preserving, stabilizing, wetting or emulsifying agents, salts for varying the osmotic pressure or buffers. They can also contain other therapeutically valuable substances. Antibiotic 1745A/X can be administered at dosages adjusted to individual requirements and fitted to the pharmaceutical exigencies of the situation.

The following examples are illustrative but not limitative of the present invention. All temperatures given are in degrees centigrade.

EXAMPLE 1

Preparation of Erythromycin A oxime N-oxide

To 53.6 g (0.07 mole) of erythromycin A oxime [Massey et al., *Tetrahedron Letters*, 157 (1970)] in 2150 ml methanol was added 1300 ml (1.1 mole) of 3% $H_2O_2$ and the solution was left at room temp for 19 hr. Most of the methanol was removed in vacuo and the crystalline product which separated was filtered and air dried. Tlc showed a single spot slower moving than the starting material. Recrystallization from MeOH—$H_2O$ yielded the above-named product, mp 181°–183°.

EXAMPLE 2

Preparation of 3'-De-(dimethylamino)-3',4'-dehydroerythromycin A oxime

Erythromycin A oxime N-oxide (5.00 g, 6.5 mmole) was pyrolyzed for 3 hr at 155°/0.1 mm in a slowly spinning flask. Tlc revealed a major spot faster moving than the starting material along with two minor impurities. The product was dissolved in methanol, decolorized with charcoal and crystallized from MeOH—$H_2O$ to yield the above-named product, mp 155°–158°.

EXAMPLE 3

Preparation of Erythronolide A oxime

A solution of 22.55 g (0.032 mole) of 3'-de-(dimethylamino)-3',4'-dehydroerythromycin A oxime in 1.5 l of 3% HCl in methanol was left at room temp for 21 hr. The methanol was removed in vacuo, EtOAc was added to the residue and the solution was washed with dilute $NaHCO_3$ solution. After drying, the solution was stirred briefly with charcoal and concentrated to dryness. Tlc revealed a major spot much slower moving than the starting material, several minor impurities and two fast moving spots. Two crystallizations from $(CH_3)_2CO$—$C_6H_{14}$ gave the above-named product, mp 236°–239°.

EXAMPLE 4

Preparation of Antibiotic 1745A/X

*Streptomyces antibioticus*, ATCC 11891, was streaked on slants of SP5 agar (yeast extract 1 g., beef extract 1 g., tryptose 2 g., $FeSO_4$ trace, glucose 10 g., agar 15 g., distilled water 1 liter-pH adjusted to 7.2) and incubated at 28° for 5 days. One slant was then washed with 10 ml of thermoactinomyces Beer Medium VI (*J. Appl. Microbiol.*, 9, 394–399, 1961) and 3 ml of this spore suspension was inoculated into 100 ml. of the same broth in cotton plugged 400 ml. Erlenmeyer flasks. These were grown at 28° and 250 RPM on a 2 inch stroke New Brunswick rotary shaker for 2 days. The flask contents were pooled, and 200 ml. was inoculated into a stirred jar containing 10 l. fermentation broth (corn starch 15.2 g., soybean meal 15.2 g., cornsteep liquor 10 g., NaCl 3.3 g., $CaCO_3$ 5 g., distilled water 1,000 ml., pH adjusted to 6.8). The silicone antifoam agent SAG #4130 (Union Carbide) was added intermittently throughout the course of the fermentation to suppress foaming. After 6 or 7 hours of growth, 1 g. of Erythronolide A oxime dissolved in 100 ml 3A alcohol was added to the fermentation and incubation was continued as before.

The course of the fermentation was followed by measuring the antibiotic potency of supernate samples with an antibiotic standard curve on *Sarcina lutea* test plates and also by thin layer chromatography of methylene chloride extracts of supernate samples (after adjustment to pH 8.5) on silica gel plates run twice through a solvent system of $CH_2Cl_2$, 90/95% aqueous MeOH, 10/conc. $NH_4OH$, 1. These plates were bioassayed on *Bacillus sp.* 1283B in prepared agar (Bactopeptone-6 g/l., cerelose-1 g/l., N-Z amine A-4 g/l., yeast autolysate-3 g/l., beef extract-1,5 g/l and agar 15 g) by inverting the plate for ½ hour on the agar, removing the plate, and incubating the agar pan overnight at 37°. Antibiotic zones were distinguished by areas of no growth on the agar. The same plate could also be sprayed with a spray of 0.15% xanthydrol in a 12:1 mixture of concentrated hydrochloric acid and glacial acetic acid and heated for 5 minutes at 120°. During fermentation of the microorganism *Streptomyces antibioticus* ATCC 11891, under the conditions described above, this microorganism co-produces the known antibiotic oleoandomycin and antibiotic 1745A/X. If the silica gel plates are sprayed with xanthydrol, the antibiotics appear as dark pink spots against a light pink background. In this fermentation, the oleandomycin produced by the culture had an $R_f$ of about 0.7 and antibiotic 1745A/X showed an $R_f$ of about 0.5. The potency of the supernate was usually about 80δ/ml between 40 and 64 hours after dosing, at which time the jar was harvested.

The contents of the jar was centrifuged to remove the cells and the supernate was adjusted to pH 8.5 with NaOH. The supernate was extracted twice with equal volumes of $CH_2Cl_2$, which were then pooled and evaporated below 30° to about 1 liter. This concentrate was extracted three times with ½ volume of 0.01 M $H_3PO_4$ and the $CH_2Cl_2$ phase discarded. The aqueous phase was immediately adjusted to pH 9 with KOH and NaCl was added almost to saturation. This was then extracted twice with ½ volumes of $CH_2Cl_2$. The combined organic phases were evaporated under reduced pressure to yield 1.2 g of solids.

Chromatography was effected by swelling 115 g Sephadex G-25 superfine beads in the lower phase of a solvent system consisting of n-butanol/acetic acid/water: 4/1/5. The Sephadex was poured into a column, 3.8 cm ID by 68 cm, and 3 bed volumes of upper phase of the above solvent system was passed through the column. A solution of 0.56 g of the solids, obtained as described in the preceding paragraph, in 1ml. of the upper phase of the solvent mixture was applied to the column and development was effected in the same upper phase. An active fraction was obtained at an elution volume of 300-360 ml. The solvent was removed under reduced pressure to yield 152 mg of solids. These solids were dissolved in 10 ml. water and the pH was adjusted from 5.2 to 9.4 with 0.5 N NaOH.

The solution was extracted three times with 10 ml of ethyl ether and the combined organic phases were evaporated under reduced pressure to yield 115 mg of solids. The solids were dissolved in 2 ml of ether and 3 ml of hexane was added. The solvent was partially evaporated under reduced pressure until the solution became turbide. After maintaining the solution at −20°, 57 mg. of antibiotic 1745A/X as a semi-crystalline precipitate was obtained. This material was recrystallized from ethanol/water: 10/90. Bioautography of a thin layer chromatogram of these crystals indicated only one active component was present.

EXAMPLE 5

Purification of Antibiotic 1745A/X Using Counter-current Distribution

Following the procedures described in Example 4 above, several fermentations of total volume 290 l to which was added 24.5 g of erythronolide A oxime were extracted with $CH_2Cl_2$. The extracts were combined and evaporated under reduced pressure to 5 l. The concentrate was extracted twice with ½ volumes of 0.01 M $H_3PO_4$. The combined acid extracts were adjusted to pH 9.5 with 0.7 N KOH and NaCl was added to make a saturated solution; this was then extracted three times with ½ volumes $CH_2Cl_2$. The combined organic solvent extracts were evaporated under reduced pressure to yield 14 g solids.

Counter-current distribution in a 100 tube apparatus (80 ml tube volume) was effected by charging 3 g of the solid into the 1st three tubes. The solvent system consisted of the upper and lower phases obtained from the mixture n-butanol/acetic acid/water: 10/1/10 adjusted to pH 2.95 with 2 N NaOH. The activity was obtained from tubes 78-88 and the solvent mixture partially evaporated under reduced pressure to 200 ml. The pH was adjusted to 9.5 with 40% NaOH and the solution extracted four times with ½ volumes of $CH_2Cl_2$. The combined organic phases were evaporated under reduced pressure to yield 0.60 g solids. Crystallization was effected from ethanol ether to yield antibiotic 1745A/X, m.p. 146°-149°.

EXAMPLE 6

| Tablet Formulation | Per Tablet |
|---|---|
| Antibiotic 1745A/X | 500 mg |
| Corn Starch | 30 mg |
| Lactose | 88 mg |
| Gelatin | 12 mg |
| Talcum | 15 mg |
| Magnesium Stearate | 5 mg |
| Total Weight | 650 mg |

PROCEDURE

1. Antibiotic 1745A/X and lactose were thoroughly mixed in suitable blending equipment and granulated with a 10% gelatin solution.

2. The moist mass was passed through a #12 screen, and the granules were dried on paper lined trays overnight.

3. The dried granules were passed through a #14 screen and placed in a suitable mixer. The talcum and magnesium stearate were added and blended.

4. The granulation was compressed into tablets weighing approximately 650 mg. each, using punches having an approximate diameter of 12.7 mm (½"). The final tablet thickness was about 5.1 mm.

EXAMPLE 7

| Tablet Formulation | Per Tablet |
|---|---|
| Antibiotic 1745A/X | 100 mg |
| Lactose, USP | 202 mg |
| Corn Starch, USP | 80 mg |
| Amijel BO 11* | 20 mg |
| Calcium Stearate | 8 mg |

| Tablet Formulation | |
|---|---|
| | Per Tablet |
| Total Weight | 410 mg |

*A prehydrolyzed food grade corn starch. Any similar prehydrolyzed corn starch may be used. Purchased from: Corn Products Company, 10 East 56th Street, New York, New York

PROCEDURE

1. Antibiotic 1745A/X lactose, corn starch, and Amijel BO 11 were blended in a suitable mixer.

2. The mixture was granulated to a heavy paste with water and the moist mass was passed through a #12 screen. It was then dried overnight at 110° F.

3. The dried granules were passed through a #16 screen and transferred to a suitable mixer. The calcium stearate was added and mixed until uniform.

4. The mixture was compressed at a tablet weight of 410 mg. using tablet punches having a diameter of approximately ⅜". (Tablets may be either flat or biconvex and may be scored if desired.)

EXAMPLE 8

| Tablet Formulation | |
|---|---|
| | Per Tablet |
| Antibiotic 1745A/X | 25 mg |
| Dicalcium Phosphate Dihydrate, Unmilled | 175 mg |
| Corn Starch | 24 mg |
| Magnesium Stearate | 1 mg |
| Total Weight | 225 mg |

PROCEDURE

1. Antibiotic 1745A/X and corn starch were mixed together and passed through a #00 screen in Model "J" Fitzmill with hammers forward.

2. This premix was then mixed with dicalcium phosphate and one-half of the magnesium stearate, passed through a #1A screen in Model "J" Fitzmill with knives forward, and slugged.

3. The slugs were passed through a #2A plate in a Model "D" Fitzmill at slow speed with knives forward, and the remaining magnesium stearate was added.

4. The mixture was mixed and compressed.

EXAMPLE 9

| Capsule Formulation | |
|---|---|
| | Per Capsule |
| Antibiotic 1745A/X | 50 mg |
| Lactose USP | 125 mg |
| Corn Starch, USP | 30 mg |
| Talc, USP | 5 mg |
| Total Weight | 210 mg |

PROCEDURE

1. Antibiotic 1745A/X was mixed with lactose and corn starch in a suitable mixer.

2. The mixture was further blended by passing through a Fitzpatrick Comminuting Machine with a #1A screen with knives forward.

3. The blended powder was returned to the mixer, the talc added and blended thoroughly.

4. The mixture was filled into #4 hard shell gelatin capsules on a Parke Davis capsulating machine.

EXAMPLE 10

| Tablet Formulation | |
|---|---|
| | Per Tablet |
| Antibiotic 1745A/X | 200 mg |
| Dicalcium Phosphate Dihydrate, Unmilled | 235 mg |
| Corn Starch | 70 mg |
| FD&C Yellow #5 - Aluminum Lake 25% | 2 mg |
| Durkee 117 | 25 mg |
| Calcium Stearate | 3 mg |
| Total Weight | 535 mg |

PROCEDURE

1. All the ingredients were mixed thoroughly and Fitzed (Model D) using a #1A screen, medium speed.

2. The mixture was remixed and slugged.

3. The slugs were screened on an Oscillator through a #14 mesh screen and compressed on an "E" machine.

EXAMPLE 11

| Capsule Formulation | |
|---|---|
| | Per Capsule |
| Antibiotic 1745A/X | 250 mg |
| Lactose | 60 mg |
| Corn Starch | 35 mg |
| Magnesium Stearate | 5 mg |
| Total Weight | 350 mg |

PROCEDURE

1. All of the ingredients were mixed until thoroughly blended in a suitable size container.

2. The powder was filled into #2, two-piece, hard shell gelatin capsules to an approximate fill weight of 350 mg. using a Parke Davis capsulating machine. (Any similar type machine may be used).

We claim:

1. Antibiotic 1745A/X characterized as follows:
   (a) melting point 146°–149° C.;
   (b) analysis: carbon, 58.69%; hydrogen, 9.26%; nitrogen, 3.45%; oxygen, 28.60% (by difference);
   (c) a characteristic infrared absorption spectrum as shown in accompanying FIG. 1;
   (d) a characteristic nuclear magnetic resonance spectrum as shown in accompanying FIG. 2;
   (e) a low resolution mass spectrum which shows a molecular ion at m/e 734 and major fragment peaks at 701, 649, 617, 573, 560, 546, 462, 416, 398, 251, 174, 158 and 145.

* * * * *